(12) United States Patent
Iijima et al.

(10) Patent No.: US 7,537,786 B2
(45) Date of Patent: May 26, 2009

(54) COMPLEX OF DRUG-CARBON NANOHORN AND A PROCESS FOR PRODUCING THE COMPLEX

(75) Inventors: Sumio Iijima, Aichi (JP); Masako Yudasaka, Ibaraki (JP); Kumiko Ajima, Ibaraki (JP); Tatsuya Murakami, Aichi (JP); Kiyotaka Shiba, Tokyo (JP)

(73) Assignee: NEC Corporation, Tokyo (JP)

( * ) Notice: Subject to any disclaimer, the term of this patent is extended or adjusted under 35 U.S.C. 154(b) by 505 days.

(21) Appl. No.: 11/212,645

(22) Filed: Aug. 29, 2005

(65) Prior Publication Data

US 2006/0193919 A1 Aug. 31, 2006

Related U.S. Application Data

(63) Continuation-in-part of application No. 11/170,103, filed on Jun. 30, 2005, now abandoned.

(30) Foreign Application Priority Data

Feb. 25, 2005 (JP) ............................. 2005-051816

(51) Int. Cl.
*A61K 9/14* (2006.01)
*A61K 33/24* (2006.01)
*A61K 38/16* (2006.01)

(52) U.S. Cl. ........................ 424/489; 424/649; 514/6; 977/734; 977/744; 977/906

(58) Field of Classification Search ........................ None
See application file for complete search history.

(56) References Cited

U.S. PATENT DOCUMENTS

| 6,090,363 | A | * | 7/2000 | Green et al. | ............. | 423/447.1 |
| 2004/0048744 | A1 | * | 3/2004 | Iijima et al. | ................. | 502/416 |
| 2005/0037374 | A1 | * | 2/2005 | Melker et al. | .................. | 435/6 |

OTHER PUBLICATIONS

Sumio Iijima; Carbon nanotubes: past, present, and future; 2002; Elsevier, Physica B, vol. 323, pp. 1-5.*
Sanjeeb K. Sohoo and Vinod Labhasetwar; 2003; Nanotech approaches to drug delivery and imaging, Elsevier, Drug Discovery Today, vol. 8 No. 24, pp. 1112-1120.*
Tatsuya Murakami, Kumiko Ajima, Jin Miyawaki, Masako Yudasaka, Sumio Iijima, Kiyotaka Shiba; 2004; American Chemical Society, Molecular Pharmaceutics, vol. 1 No. 6 pp. 399-405.*
Sun, ML; Wen, YM; Wang, CM; Li, LJ; Wang, XY; 2004; Hua Xi Kou Qiang Yi Xue Za Zhi (3)(Abstract Only); Englis Abstract retrieved from: http://www.ncbi.nlm.nih.gov/sites/entrez (PMID: 15293458).*

(Continued)

*Primary Examiner*—Johann R Richter
*Assistant Examiner*—Ivan Greene
(74) *Attorney, Agent, or Firm*—Dickstein Shapiro LLP

(57) ABSTRACT

The present invention provides a carbon nanohorn complex that is excellent in characteristics of adsorption or inclusion of drugs and release, in particular, a sustained release of drugs as a novel drug carrier in drug delivery systems, as well as a process for producing the complex. The complex of drug and carbon nanohorns comprises a steroidal or metal-containing drug being adsorbed onto the oxidized carbon nanohorns, or included in pores opened thereof.

5 Claims, 14 Drawing Sheets

OTHER PUBLICATIONS

Tiangui Huang, Yanhua, Jixin Wang, Junxin Huang, Dingxin Liu, Shucong Mong; Pingyangmycin as a (99m)Tc Carrier in Tumor Localization, 1995, Pergamon, Nucl. Med. Biol. vol. 22 No. 4 pp. 537-542.*

S. Iijima, et al.; "Nano-aggregates of single-walled graphitic carbon nano-horns"; Chemical Physics Letters; vol. 309; Aug. 13, 1999; pp. 165-170.

E. Bekyarova, et al.; "Oxidation and Porosity Evaluation of Budlike Single-Walled Carbon Nanohorn Aggregates"; Langmuir; vol. 18; 2002; pp. 4138-4141.

Elena Bekyarova, et al.; "Controlled Opening of Single-Walled Carbon Nanohorns by Heat Treatment in Carbon Dioxide"; The Journal of Physical Chemistry; vol. 107(19); May 15, 2003.

Anya Kuznetsova, et al.; "Enhancement of adsorption inside of single-walled nanotubes: opening the entry points"; Chemical Physics Letters; vol. 321; Apr. 28, 2000; pp. 292-296.

Masako Yudasaka, et al; "Nano-extraction and nano-condensation for $C_{60}$ incorporation into single-wall carbon nanotubes in liquid phases"; Chemical Physics Letters; vol. 380; 2003; pp. 42-46.

Murakami et al., Molecular Pharmaceutics, vol. 1, No. 6, pp. 399-405 (2004).

* cited by examiner

COMPLEX OF DRUG-CARBON NANOHORN AND A PROCESS FOR PRODUCING THE COMPLEX

CROSS REFERENCE TO RELATED APPLICATIONS

This application is based on and claims priority to U.S. patent application Ser. No. 11/170,103, filed Jun. 30, 2005, and Japanese Application No. 2005-051816 filed Feb. 25, 2005, both entitled A COMPLEX OF DRUG-CARBON NANOHORN AND A PROCESS FOR PRODUCING THE COMPLEX, the entire disclosures of which is hereby incorporated by reference.

FIELD OF THE INVENTION

The present invention relates to a complex of drug and carbon nanohorns that is useful for drug delivery system and the like, and to a production process thereof.

BACKGROUND OF THE INVENTION

A variety of inorganic substances are recently studied as carriers of drug in drug delivery systems. As for such carriers, nanoparticles are particularly noted, and hydroxyapatite crystals and nanoparticles on the basis of silica and the like have been reported so far.

Under these circumstances, there has been a growing interest in a functional nanoparticle, i.e. carbon nanoparticles such as a fullerene, carbon nanotubes, and carbon nanohorns.

Among these particles, carbon nanohorns (CNH) are recently discovered as a new type of carbon nanoparticles during the study of carbon nanotube preparation by the present inventors (see Non-patent Document 1). It has been found by using transmission electron microscopy (TEM), that the particles are nanostructured spherical aggregates of graphitic tubes of which the diameter is about 80 nm and most are attached with conical caps (horns). Each horn consists of completely closed single-wall graphitic sheet and its diameter is 2 to 3 nm, which is much larger than the 1.4 nm of typical single-wall carbon nanotubes.

In addition, an oxidation treatment produced nanowindows on the top or in the side wall of the horn, and it has been confirmed that various molecules can infiltrate into the inner space of the horn through the hole (see Non-patent Document 2). This enables to use the inner wall and internal cavity of the horn as a capture site of a substance, and greatly enlarges the surface area of the oxidized carbon nanohorns compared to non-oxidized carbon nanohorns. In fact, nitrogen gas can be not only adsorbed onto the interstices of the individual oxidized sigle-walled carbon nanohorns (SWNHox), but also included in the internal cavities of the horns. Diameters of the holes of side wall and top of the horn are measured as 1.58 nm and 1.17 nm, respectively on TEM photographs of SWNHox. The oxidation also introduces oxygen functional groups such as carboxylic groups and quinine groups at the pore edges of the SWNHox (see Non-patent Documents 3 and 4).

On the other hand, the present inventors also reported that the incorporation of fullerene (C60) into oxidized single-wall carbon nanotubes in liquid phase through the pores of tips and sidewalls (see Non-patent Document 5).

[Non-patent Document 1]

Iijima, S. et al., Chem. Phys. Lett. (1999) Vol. 309, pp. 165-170

[Non-patent Document 2]

Bekyarova, E. et al., Langmuir (2002) Vol. 18, pp. 4138-4141

[Non-patent Document 3]

Bekyarova, E. et al., J. Phys. Chem. (2003) Vol. 107, pp. 4479-4484

[Non-patent Document 4]

Kuznetsova, A. et al., Chem. Phys. Lett. (2000) Vol. 321, pp. 292-296

[Non-patent Document 5]

Yudasaka M. et al., Chem. Phys. Lett. (2003) Vol. 380, pp. 42-46

SUMMARY OF THE DISCLOSURE

Disclosures of the above Non-patent Documents 1 to 5 are in entirety incorporated herein by reference. The present inventors have been studied the application of carbon nanohorns (CNH) and their oxidized and porous form (CNHox) as a novel drug carrier in drug delivery systems based on the previous findings thereof. Thus, it is an object of the present invention to provide a complex of carbon nanohorn as a novel drug carrier, which is excellent in characteristics of drug adsorption or inclusion and releasing properties, in particular, a sustained release of drugs, as well as a process for producing the complex.

To overcome the problems describe above, the present application provides following inventions.

[1] A complex of drug and carbon nanohorns, which complex comprises a steroidal or metal-containing drug being adsorbed onto or included in oxidized porous carbon nanohorns.

[2] The complex of drug and carbon nanohorns, exhibiting a sustained release of the drug into an aqueous solution of phosphate-buffered saline.

[3] The complex of drug and carbon nanohorns, wherein the drug is a compound having a melting point of not higher than 300° C.

[4] The complex of drug and carbon nanohorns, wherein the steroidal drug comprises dexamethasone or an ester derivative thereof.

[5] The complex of drug and carbon nanohorns, wherein the metal-containing drug is cisplatin or bleomycin. Alternatively, the metal-containing drug may be replaced with an anti-cancer drug containing no metal atom.

[6] A process for producing any one of the drug-carbon nanohorn complexes described above, comprising preparing an oxidized porous carbon nanohorns, and mixing the carbon nanohorns with the drug in a mixed solvent of a polar solvent and water.

[7] The process for producing a complex of drug and carbon nonohorns, comprising heat-treating the oxidized porous carbon nanohorns at a temperature in the range between 200° C. and 1800° C. under the hydrogen atmosphere, and then mixing the carbon nanohorn with the drug in a mixed solvent of a polar solvent and water.

The meritorious effects of the present invention are summarized as follows.

According to the present invention, there is provided a novel complex of carbon nanohorns that is capable of using as a drug carrier in drug delivery systems, and is excellent in characteristics of drug adsorption or inclusion and releasing properties, in particular, a sustained release of drugs, as well as a simple process for producing the complex.

PREFERRED EMBODIMENTS OF THE INVENTION

Figure 1:
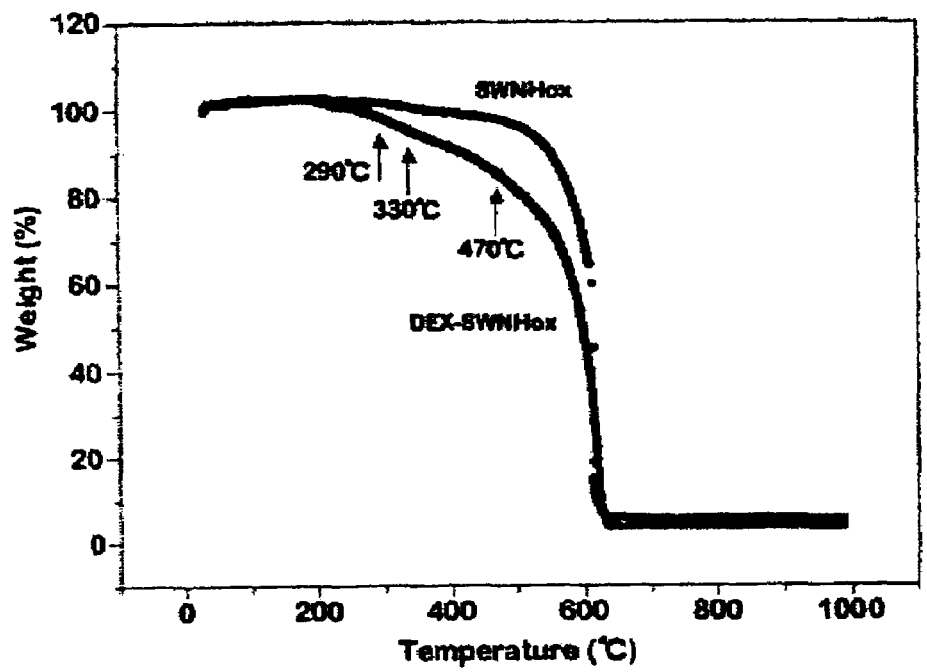
FIG. 1 illustrates the results of thermogravimetric analysis (TGA) of DEX-CNHox at rate of 10 deg/min under $O_2$ stream.

The present invention has the technical features described above, and is explained in its embodiments as follows.

In the drug-carbon nanohorn complex of the present invention, the term "drug" refers to a pharmaceutical, an animal drug or the like. The drug comprises a steroidal drug, a metal-containing drug, and an anti-cancer drug. These drugs are adsorbed onto or included in the oxidized and porous carbon nanohorns.

As used herein, the phrase "oxidized porous carbon nanohorns" means carbon nanohorns having pores opened, obtained by oxidizing carbon nanohorn aggregates according to the process developed by the present inventors.

By selecting a condition of the oxidation treatment, it is capable of changing the degree of pores opened, for example, the number, size and surface property of the generated nanopores, and controlling characteristics of drug adsorption or inclusion and releasing properties, in particular, a sustained release of drugs. That is, the pore size of the oxidized porous carbon nanohorns can be freely adjusted in a range from about 0.2 nm to about 3 nm, thus it is capable to prepare carbon nanohorns with pores of the preferable size in accordance with the molecular size and physical property of the drug that is included and complexed.

The drug release property can be also controlled by heat-treatment of the oxidized porous carbon nanohorns at a temperature not lower than 200° C. under the hydrogen atmosphere, before adsorbing the drug to the porous carbon nanohorns. The heat-treatment at a temperature lower than 200° C. is not preferable for the reason that the control effect may not be sufficient. An upper limit to the temperature of the heat-treatment is not limited as far as the sustained release is possible, but, in practical, it may be 1800° C.

As a means for adsorption and inclusion of the drug, it can be achieved by mixing the carbon nanohorns with the drug in a liquid phase. As a liquid phase, an appropriate solvent can be selected, and a mixed solvent of a polar solvent such as alcohols, DMF, DMSO and acetonitrile, and water is preferably selected. It is preferable to use a mixed solvent comprising an alcohol, in particular, ethanol and water in a ratio of 20 to 80% by volume and 80 to 20% by volume, respectively, and to mix each other under a temperature between 5° C. and 30° C.

In a preferred embodiment of the present invention, the oxidized porous carbon nanohorns (CNHox) adsorb or include dexamethasone (DEX) used for an anti-inflammatory drug with a maximum binding capacity of 200 mg/g in a mixture of equal volumes of ethanol and water. The DEX-CNHox complex exhibits a sustained release of DEX into an aqueous solution of phosphate-buffered saline. Treatment of mouse osteoblast MCT3T-E1 cell with DEX-CNHox accelerates the expression of alkaline phosphatase in the cell, which is an essential function of DEX on cells, and showed no toxicity by the complexation. These results indicate that the CNHox is useful for a biocompatible drug carrier for the first time.

In one embodiment of the inventive complex comprising a drug being adsorbed onto or included in the oxidized porous carbon nanohorns, the drug is preferably a compound having a melting point of not higher than 300° C. The steroidal drug includes, for example, but is not limited to, dexamethasone, prednisolone, betamethasone, paramethasone, hydrocortisol, cortisol and the like, or ester derivatives thereof. The metal-containing drug includes, but is not limited to, cisplatin (platinum coordination compound) and bleomycin (iron coordination compound) known as anti-cancer drugs, and Strontium Ranelate known as a therapeutic drug for osteoporosis. In addition, the anti-cancer drugs are, for example, cisplatin (includes carboplatin, oxaliplatin, spiroplatin, isoplatin and the like), camptothecin, actinomycin, mitomycin C, adriamycin (doxorubicin), 5-fluorouracil (5-FU), daunorubicin, etoposide or mitoxantrone. These anti-cancer drugs can be imparted a property of sustained release by being included in the carbon nanohorns to reduce the toxicity to the normal cells. On the other hand, the drug included in the carbon nanohorn can exhibit a long-acting efficacy by accumulating in cancer cells. Thus, in another embodiment of the present invention, there is provided a complex of drug and carbon nanohorn, which complex comprises a steroidal drug, metal-containing drug or anti-cancer drug being adsorbed onto or included in the oxidized porous carbon nanohorns, wherein the release of the drug from the complex is controlled.

The present invention is explained in more detail by the reference of the following examples, however, these examples do not restrict the scope of the present invention.

EXAMPLE 1

<Materials and Methods>

1) Materials

The carbon nanohorn aggregates (CNH) and their oxidized porous form (CNHox) were made based on the above-mentioned reports (see Non-patent Documents 1-2). Briefly, the oxidization of the CNH was conducted in flowing pure oxygen (760 Torr) in a quartz tube at 580° C. for 10 min.

Dexamethasone (DEX), β-glycerophosphate, ascorbic acid and SIGMA FAST (registered trade-mark) p-nitrophenyl phosphate tablet set were obtained from Sigma. Ethanol (EtOH) was obtained from Wako. [1,2,4-$^3$H] dexamethasone was purchased from Amersham Bioscience. Recombinant human bone morphogenetic protein-4 (rhBMP-4) was obtained from Genzyme/TECHNE. Protein quantitative assay kit (DC Protein Assay Kit) was obtained from Bio-Rad. Fetal bovine serum (FBS) was purchased from JRH Bioscience. α-minimum essential medium (α-MEM), Dulbecco's phosphate-buffered saline (PBS) and trypsin-EDTA (0.05% trypsin, 0.53 mM EDTA-4Na) were obtained from Invitrogen. Penicillin and streptomycin were purchased from Banyu Pharmaceutical CO., LTD and Meiji Seika Kaisha, LTD, respectively. Normal cell culture dishes were purchased from IWAKI.

2) Adsorption or Inclusion of DEX in CNHox

CNHox (100 μg/ml) and DEX (1000 μg/ml) were added to EtOH/$H_2O$ (50/50), the resultant mixture was incubated at room temperature overnight. Then the mixture was centrifuged at 15,000 rpm for 5 min. By eliminating the supernatant, dexamethasone-CNHox complex (DEX-CNHox) was obtained as residue. DEX-CNHox was dried under vacuum and then was used for following bioassays. $^3$H-labeled DEX was used for estimating required immersion time for maximum DEX adsorption or inclusion in CNHox, maximum binding capacity and affinity of CNHox and CNH for DEX. And $^3$H-labeled DEX was also used to prepare $^3$H-labeled DEX-CNHox for in vitro release assay.

3) Thermogravimetric Analysis (TGA)

Sequential thermogravimetric analysis was conducted under pure $O_2$ gas flowing at 100 cm$^3$/min and at a heating rate of 10° C./min from room temperature to 1000° C. using Hi-Res TGA 2950 Thermogravimetric analyzer (TA Instruments).

4) In vitro Release of DEX from DEX-Binding CNHox $^3$H-labeled DEX-CNHox was dispersed in PBS (0.005 wt %) and then incubated at 37° C. At appropriate time, this suspension was centrifuged at 15,000 rpm for 5 min, and the supernatant was retrieved. The amount of $^3$H-DEX in the supernatant was measured using LS6500 scintillation counter (Beckman). In the case of cumulative release experiments, the supernatant was immediately replaced with fresh PBS at each sampling point, and then $^3$H-labeled DEX-CNHox was resuspeded in PBS (0.005 wt %) and incubated at 37° C. until next sampling point.

5) Cell Culture

Mouse osteoblastic cell (MC3T3-E1) lines were generously provided by Dr. Imamura (Cancer Institute, Japanese Foundation For Cancer Research). MC3T3-E1 cells were maintained in α-minimum essential medium (α-MEM) supplied with 5% FBS, 100 μg/ml penicillin and 100 U/ml streptomycin in continuous culture at 37° C. in a humidified atmosphere of 5% $CO_2$ and 95% air, and these cells were passaged every 3-4 days.

6) ALP (Alkaline Phosphatase) Activity Assay

MC3T3-E1 cells were plated at 26,000 cells/cm$^2$ in 24 well plates and were grown until confluent. Next, the culture medium was exchanged with differentiation-inducing medium which consisted of α-MEM, 5% FBS, 100 U/ml penicillin, 100 μg/ml streptomycin, 50 μM ascorbic acid, 10 mM β-glycerophosphate and 20 ng/ml rhBMP-4. And then differentiation-inducing medium were added with CNHox or DEX-CNHox (0.2, 1, 2, 10, 20 μg/ml). The cells cultured for another 10 days while differentiation-inducing medium was refreshed every 3-4 days. The medium was changed carefully so that CNHox or DEX-CNHox which adhered to the cells were not sucked in.

For ALP activity assay, the medium was removed, and the cells were washed 3 times with TBS (20 mM Tris pH7.4, 150 mM NaCl), then harvested into 250 μl of TBS (contaning 0.2% Triton X-100) by scraping them on ice, and sonicated on ice for 5 min. And the resulting cell lysates were centrifuged at 15,000 rpm at 4° C. for 10 min, and aliquots of supernatant were taken up for ALP assay and protein assay. The supernatant was mixed with p-nitro phosphate according to the manufacture's protocol, and the amount of p-nitrophenol released in 10 min was assessed by spectrophotometry (405 nm) with model 550 microplate-reader (Bio-Rad). Protein concentration of supernatant was assessed with protein quantitative assay kit (DC Protein Assay Kit) by the Lowry method. ALP activity was estimated as ratio of amount of p-nitrophenol to total protein concentration.

<Results>

<1> Adsorption or Inclusion of Dexamethasone (DEX) in Oxidized Single-wall Carbon Nanohorn (CNHox)

CNHox supernatant and DEX solution were mixed in EtOH/$H_2O$ (50/50), and the mixture was incubated overnight at room temperature. The resulting solid fractions were examined with thermogravimetric analyzer (TGA). FIG. 1 shows the TGA profile of DEX-CNHox complex, which was prepared from 100 μg/ml of CNHox and 1000 μg/ml initial concentration of DEX, and of CNHox only. The weight loss of DEX-CNHox was observed at five steps around 210, 290, 330, 470 and 610° C. The weight loss of around 210 and 610° C. was caused by evaporation of the solvent and decomposition of CNHox, respectively. It was clearly proven that DEX were adsorbed onto or included in CNHox, because the weight loss of around 290, 330, and 470° C. was peculiar for DEX-CNHox, and corresponding endothermic peak was almost equal to the peak of pure DEX. The total amount of adsorbed or included DEX in CNHox was about 200 mg for 1 g CNHox.

Adsorption or inclusion of DEX was further estimated in detail using $^3$H-labeled DEX. The amount of adsorbed or included DEX referred as function of immersion time was saturated within a few minutes of incubation. Such rapid saturation was also observed in absorption of cisplatin onto hydroxyapatite crystals (Barroug et al., J. Orthop. Res., 20, 274-280). CNHox was then immersed for 1 hour at least in order to shorten the immersion time and to avoid the incomplete adsorption or inclusion.

Figure 2:
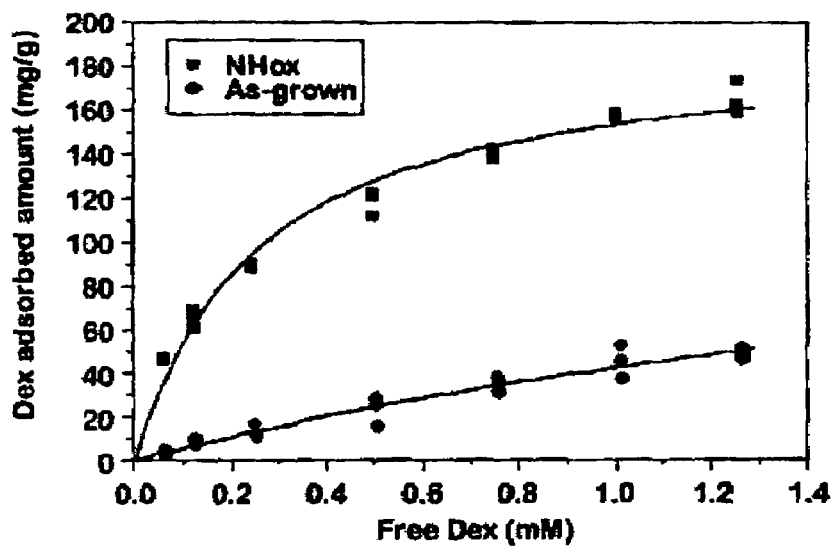
FIG. 2 shows Langmuir adsorption isotherms describing adsorption of DEX by CNHox and CNH in a 1:1 ethanol/$H_2O$ mixture: plotted is the amount of DEX adsorbed vs the steady-state drug concentration.

It was examined that the relationship between DEX concentration remained in the solution and amount of DEX adsorbed onto or included in carbon nanohorns under the condition of EtOH/$H_2O$ (50/50). CNHox or CNH (0.1 mg/ml) was mixed with DEX (containing various concentration of $^3$H-labeled DEX) in EtOH/H$_2$O (50/50), the mixture was incubated overnight, and carbon nanohorns absorbing or including DEX were taken as residue after centrifugation of the mixture. FIG. 2 shows the result of quantification for adsorption or inclusion of DEX in CNHox or CNH measured using liquid scintillation counter.

The black square and the black circle in FIG. 2 represent CNHox and CNHC, respectively.

As shown in FIG. 2, the amount of DEX adsorbed onto or included in CNHox increased with increasing DEX concentrations in the solution in an equilibrium state, and thereafter the rise became gentle, and came to a plateau. The amount of DEX adsorbed by CNHoxs was determined to be 200 mg for each gram of CNHoxs in 0.5 mg/ml of DEX solution, which was approximately 6 times larger than that obtained for as-grown CNHs. The oxidized CNHs have nanowindows in their walls, through which small molecules can infiltrate into the inner space of CNHs. It has been already shown that the interior surfaces of CNHs had a stronger binding energy for H$_2$ and N$_2$, suggesting the possible contribution of the interior surfaces of the CNHoxs for the increased affinity for DEX.

<2> In vitro Release of DEX from DEX-CNHox Complex

Figure 3:
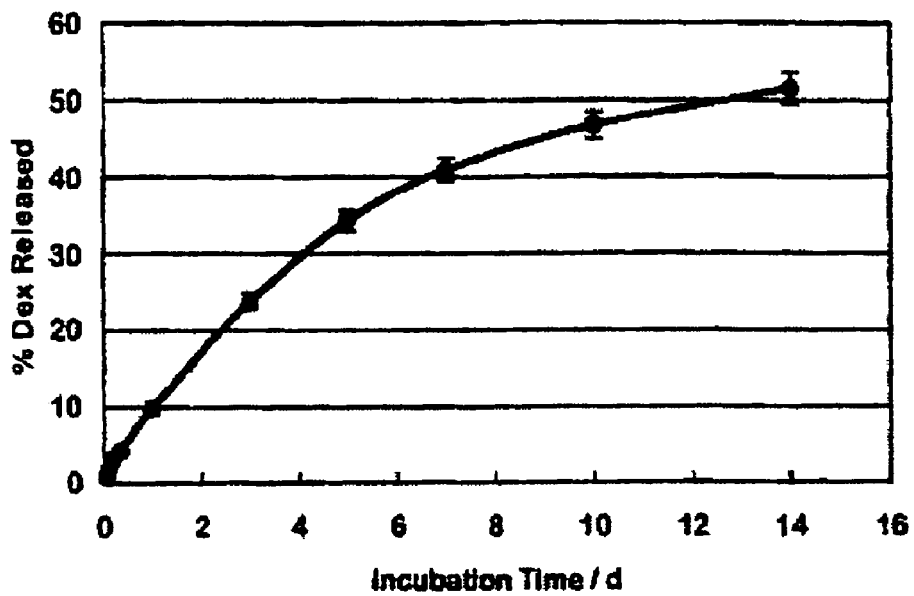
FIG. 3 illustrates the cumulative releasing efficiency of DEX from DEX-CNHox complex in PBS at 37° C.

Sustained release of drug from the drug carrier is necessary in order to be clinically useful. FIG. 3 shows the releasing efficiency of DEX from DEX-CNHox complex in PBS (pH7.4) at 37° C. The culmulative release rate of DEX from DEX-CNHox in PBS at 37° C. as shown in FIG. 3 was measured with the following steps. After DEX-CNHox prepared with $^3$H-labeled DEX was dispersed at 0.005 wt % in PBS, the mixture was incubated at 37° C., and PBS was refreshed at each indicated time, and then, the released DEX quantity in taken out PBS was measured using the liquid scintillation counter. The amount of DEX released upto each indicated time was shown as percentages (%) of total DEX bound to DEX-CNHox. In FIG. 3, DEX was slowly released from the complex in PBS. The release was almost proportional to the incubation time at the initial stage, then the release became gradually slow, and reached the plateau. 52% of total amount of first DEX-CNHox complex was released by the end of 2 weeks. Peculiar surface characteristics of CNHox seem to contribute to control the sustained release of DEX from DEX-CNHox.

When DEX-CNHox was incubated in PBS at 37° C. for 3 days without refreshing PBS, 14% of DEX bound to DEX-CNHox was released. This amount was even less than the amount of 24% measured in the cumulative release experiment in which PBS was refreshed 5 times in the first 3 days (FIG. 3). This indicates that the dynamic phase of the DEX release from DEX-CNHox in PBS may be also affected by the solubility of DEX (10 mg/100 ml H$_2$O at 25° C.) in PBS.

<3> Biological Activities of DEX-CNHox Complex in vitro

Figure 4:
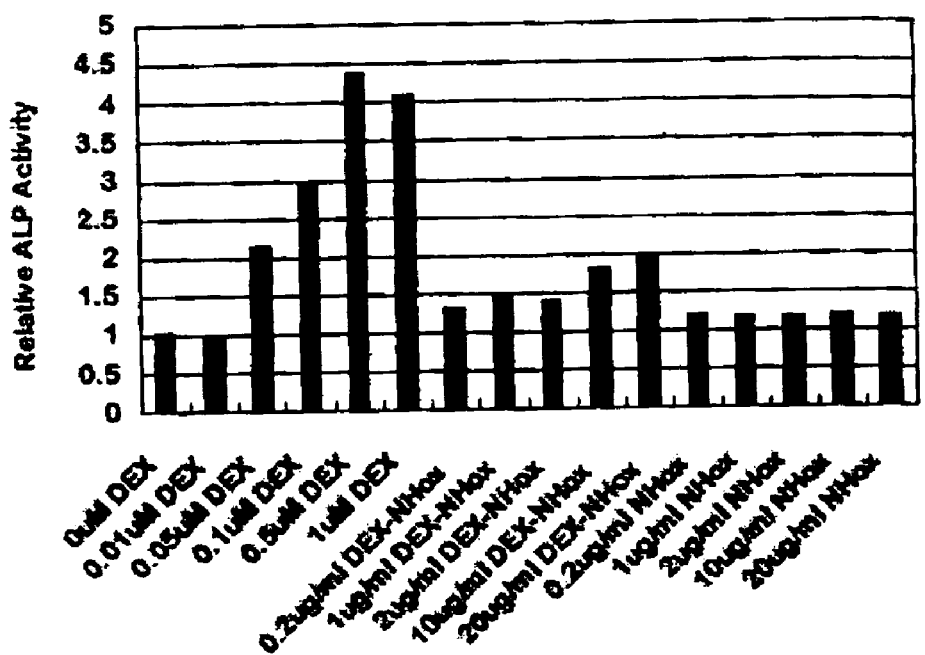
FIG. 4 illustrates the effects of DEX-CNHox and CNHox for alkaline phosphatase (ALP) activities.

Next, the biological activity of DEX-CNHox complex in vitro was examined using the osteoblast MC3T3-E1 cells. DEX is a synthetic glucocorticoid, known to promote expression of alkaline phosphatase (ALP; one of the differentiation marker in the osteogenesis). On the other hand, it was reported that ALP expression of MC3T3-E1 cells increases by treating with DEX under bone morphogenetic protein 2 ((BMP)-2) which is a potent promoter of osteoblastic differentiation and osteogenesis. FIG. 4 shows the effect of DEX-CNHox and CNHox on the alkaline phosphatase (ALP) activity.

The cells were cultivated for 10 days in α-MEM which contained the mixture of 5% FBS, 50 μg/ml ascorbic acid, 10 mM β-glycerophosphate and 20 ng/ml rhBMP-4 in combination with any of DEX (0.01, 0.05, 0.1, 0.5, 1 μM) or CNHox (0.2, 1, 2, 10, 20 μg/ml) or DEX-CNHox (0.2, 1, 2, 10, 20 μg/ml). The culture medium was changed every 3-4 days without further addition of CNHox or DEX-CNHox. ALP activity was measured using p-nitrophenyl phosphate, and normalized to the protein concentration, and relative ALP activity was calculated, shown as 1 fold induction. As shown in FIG. 4, ALP activity was increased by adding DEX no less than 0.05 μM to the MC3T3-E1 cells, and this indicated that DEX was biologically active to the MC3T3-E1 cells under this culture condition.

By the CNHox treatment, there was no significant effect on ALP activity. In contrast, ALP activity was remarkably increased by the treatment of DEX-CNHox more than 2 μg/ml (FIG. 4). From these results, it was clearly demonstrated that CNHox itself had no inhibitory effect on ALP expression of the MC3T3-E1 cells, while DEX-CNHox showed the DEX proper biological activity. Furthermore, even in the treatment with the maximal dose (20 μg/ml) of CNHox, cytotoxicity was not observed.

EXAMPLE 2

Single-wall carbon nanohorn aggregates (CNH) were heated in flowing pure oxygen (760 Torr) at 570-580° C. for 15 min.

The resulting oxidized and porous carbon nanohorns (CNHox) were dispersed in water (1 mg/ml). On the other hand, cisplatin (CDDP) powder (Sigma) was dissolved at 20 mg/ml DMSO and DMF, respectively. To the above dispersion of CNHox-H$_2$O was added the cisplatin solution dropwise at 30-100° C.

The complex of CDDP and CNHox was obtained. This complex was dried at 130° C. for 3 hours, after the filtration.

Figure 5:
FIG. 5 is a HR-TEM image of CDDP-CNHox complex in Example 2.
Figure 6:
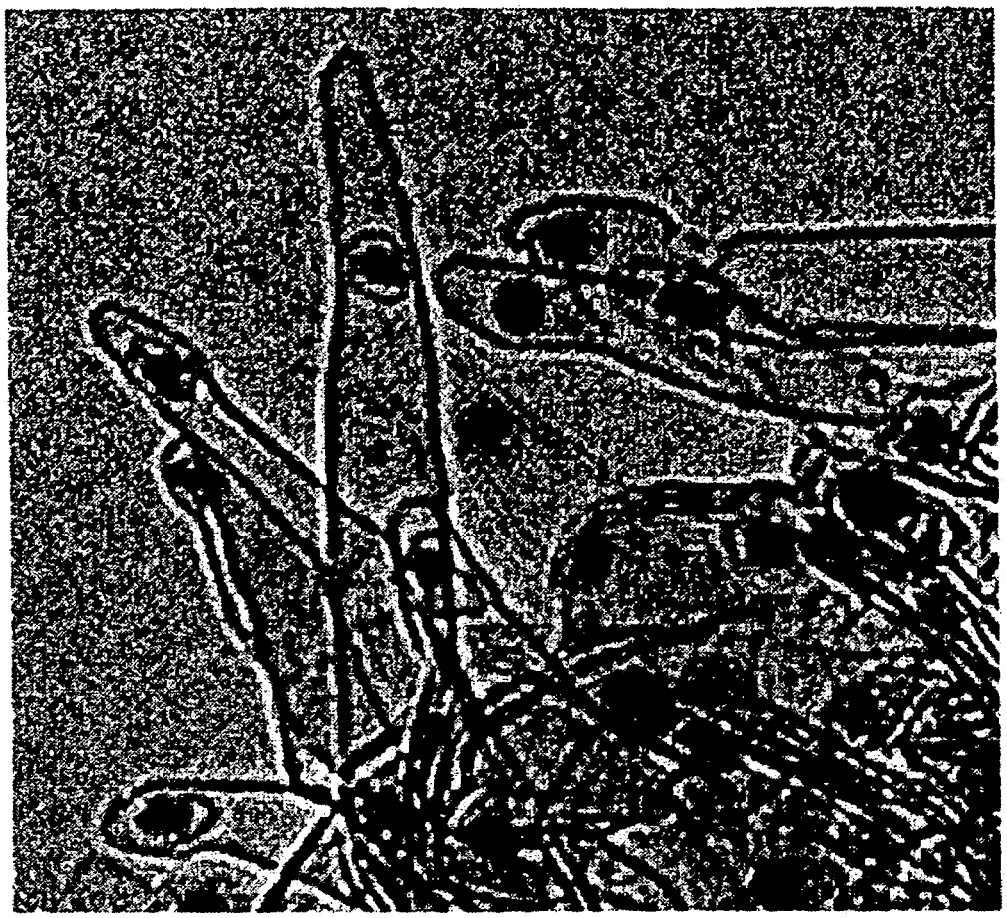
FIG. 6 is a high-resolution HR-TEM image of CDDP-CNHox complex in Example 2.
Figure 7:
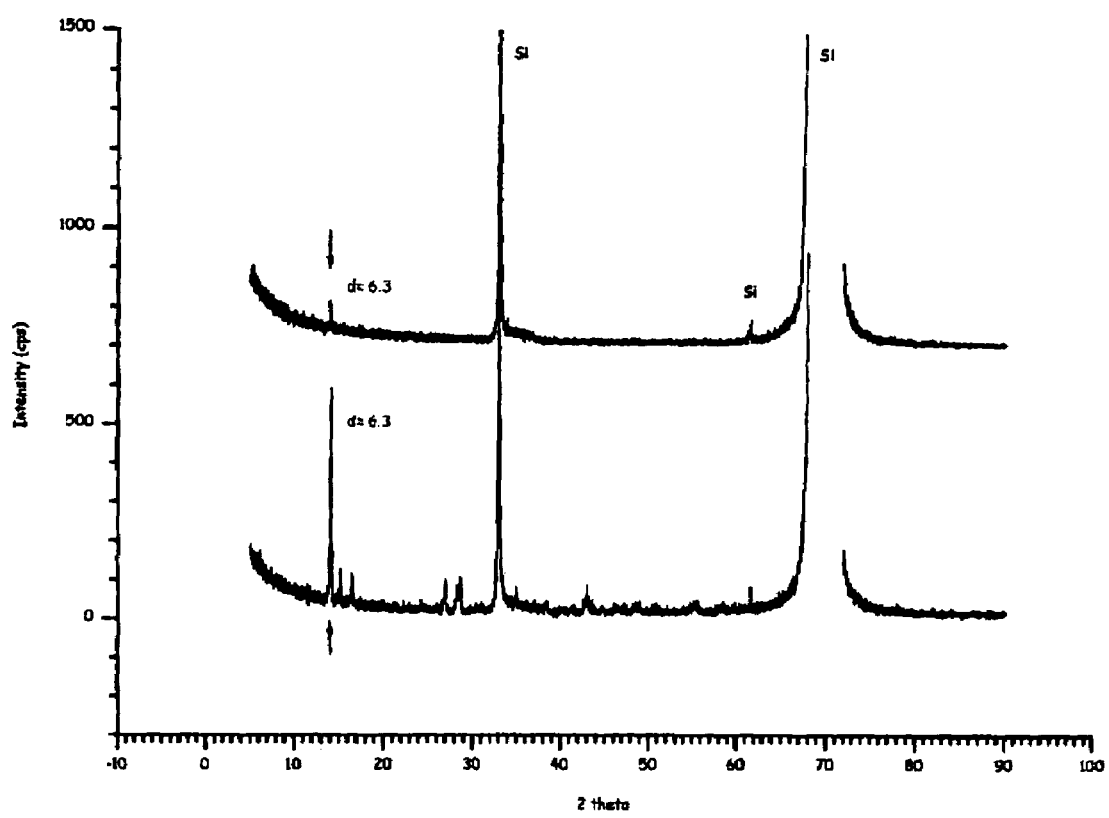
FIG. 7 shows the result of X-ray diffraction analysis for CDDP-CNHox complex in Example 2.

FIG. 5 is a HR-TEM image of this complex, and FIG. 6 is a high-resolution image thereof. Black particles indicate CDDP, and show that CDDP has been adsorbed onto or included in CNHox. FIG. 7 shows the result of X-ray analysis, and its lower and upper lines show the CDDP result and CDDP-CNHox result, respectively. The detection peak of CDDP is noted at d=6.3 Å.

EXAMPLE 3

Single-wall carbon nanohorn aggregates (CNH) were heated under pure oxygen gas flow (760 Torr) at 570-580° C. for 15 min.

1 mg of resulting oxidized and porous carbon nanohorns (CNHox) was mixed into CDDP/DMF solution (1 mg/10 mL), following DMF was entirely evaporated, and then CDDP and CNHox complex was obtained. The amount of the obtained CDDP-CNHox complex was about 0.24 mg/mg.

<1> Adsorption or Inclusion of CDDP in CNHox

Figure 8:
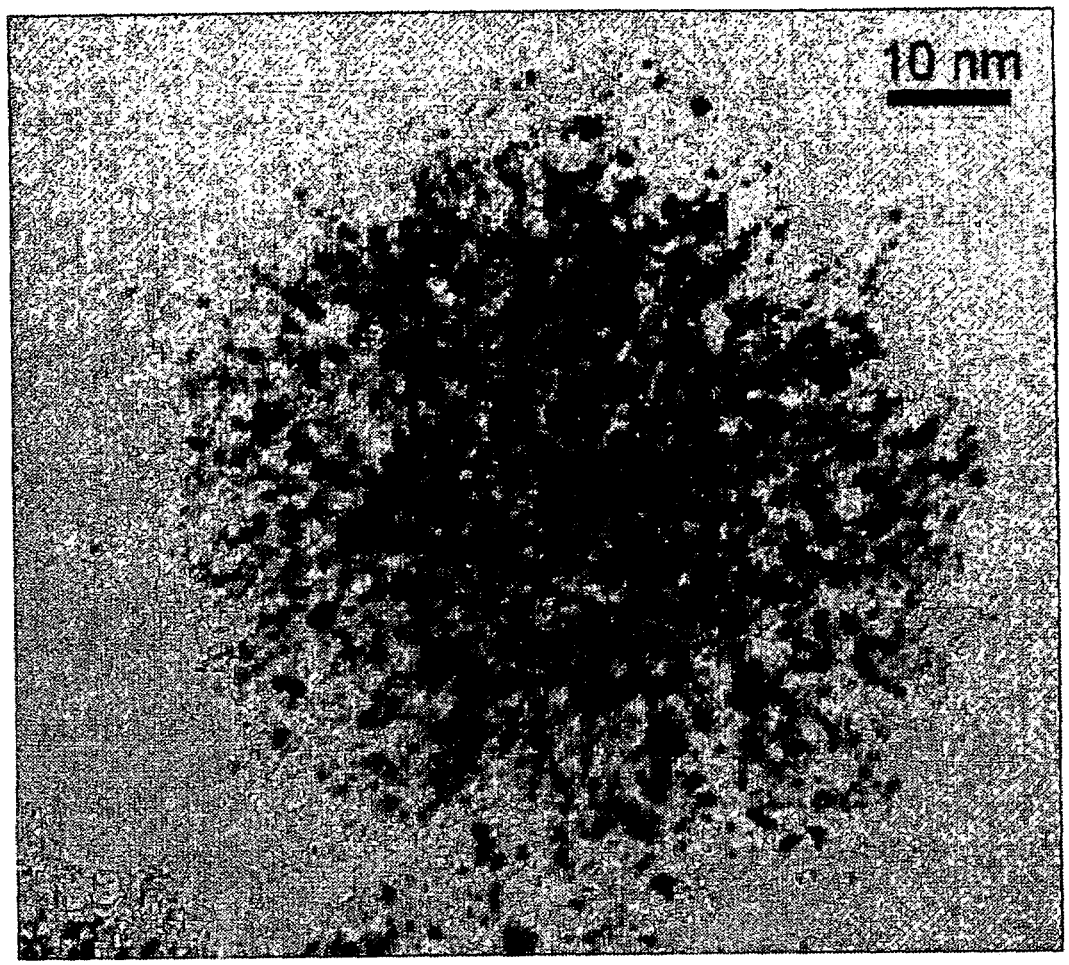
FIG. 8 is a HR-TEM image of CDDP-CNHox complex in Example 3.
Figure 9:
FIG. 9 is a high-resolution HR-TEM image of CDDP-CNHox complex in Example 3.

FIG. 8 is a HR-TEM image of this complex, and FIG. 9 is a high-resolution image thereof. Black particles indicate CDDP, and show that CDDP has been adsorbed onto or included in CNHox.

Figure 10:
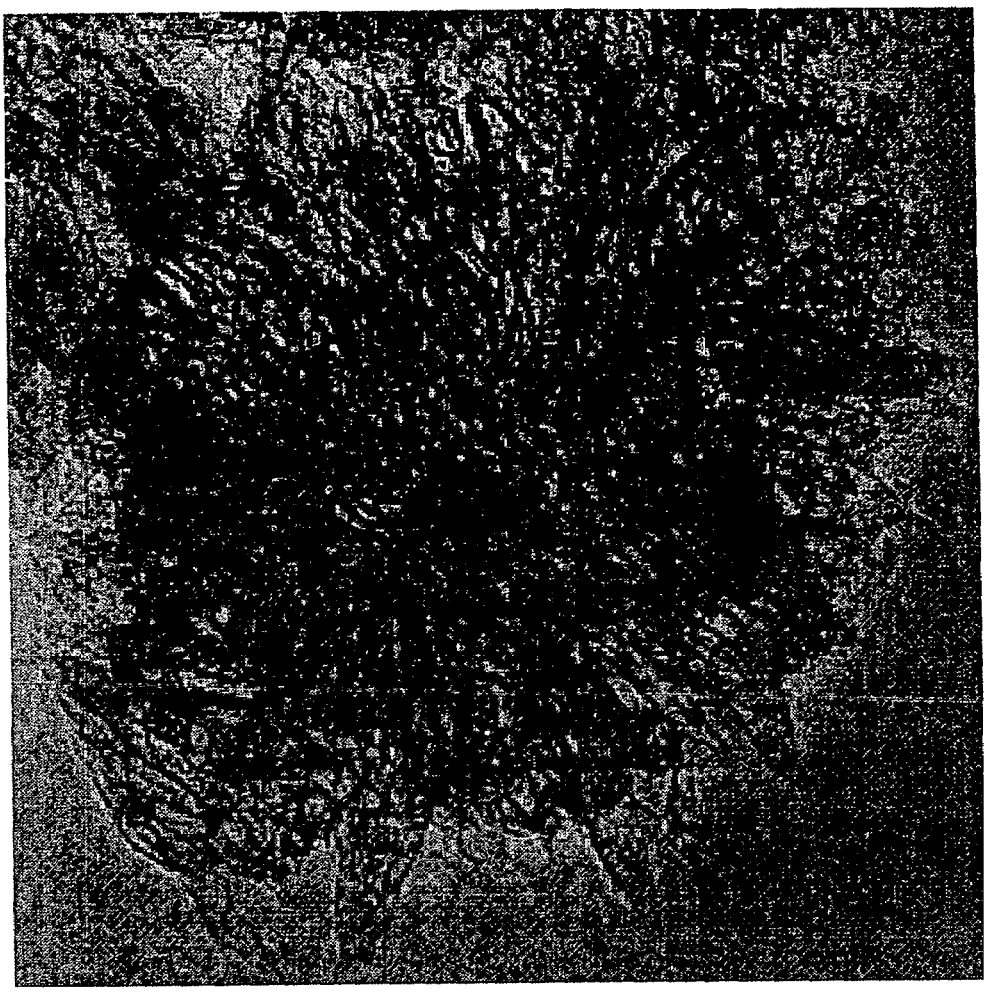
FIG. 10 is a HR-TEM image of CDDP-CNHox complex from which CDDP clusters have been released in Example 3.
Figure 11:
FIG. 11 is a high-resolution HR-TEM image of CDDP-CNHox complex from which CDDP clusters have been released in Example 3.

CDDP clusters included in the complex were released in the physiological saline, when the above-mentioned CDDP-CNHox complex was immersed in physiological saline for 10 hours. FIG. 10 is a HR-TEM image of carbon nanohorns of the CDDP-CNHox complex from which CDDP clusters were released, and FIG. 11 is a high-resolution image thereof. Black particles (CDDP) observed in FIGS. 8 and 9 were not observed in the carbon nanohorns in these figures.

Figure 12:
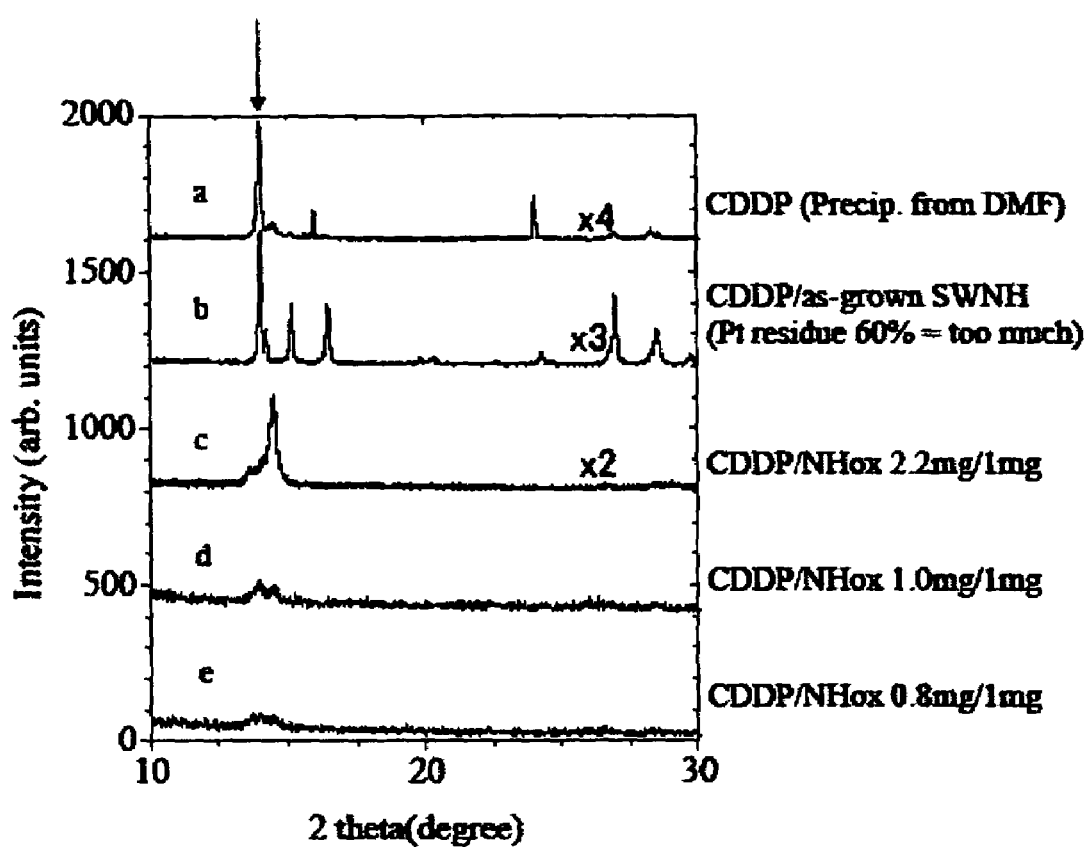
FIG. 12 shows the result of X-ray diffraction analysis in Example 3.

CDDP can be observed by X-ray diffraction, when CDDP is not included in CNH and locates outside thereof. This is because CDDP makes crystals outside of CNH or CNHox if non-oxidized and non-porous CNH is used or CDDP is excessively used. FIG. 12 shows the X-ray diffraction result. In this figure, "a" represents CDDP deposited from DMF, and "b" represents the case using CNH, and "c" represents the case using excessive CDDP. In these "a", "b" and "c", CDDP proper peaks pointed by the arrow in the figure exhibited the intensive peak strength. In the meantime, CDDP was efficiently included when the adequate quantity of CDDP was used (see "d" and "e"), and the strength of the characteristic peaks in CDDP was weak, and also the width of the peaks was narrow. This may be due to the small size of the included CDDP clusters.

Figure 13:
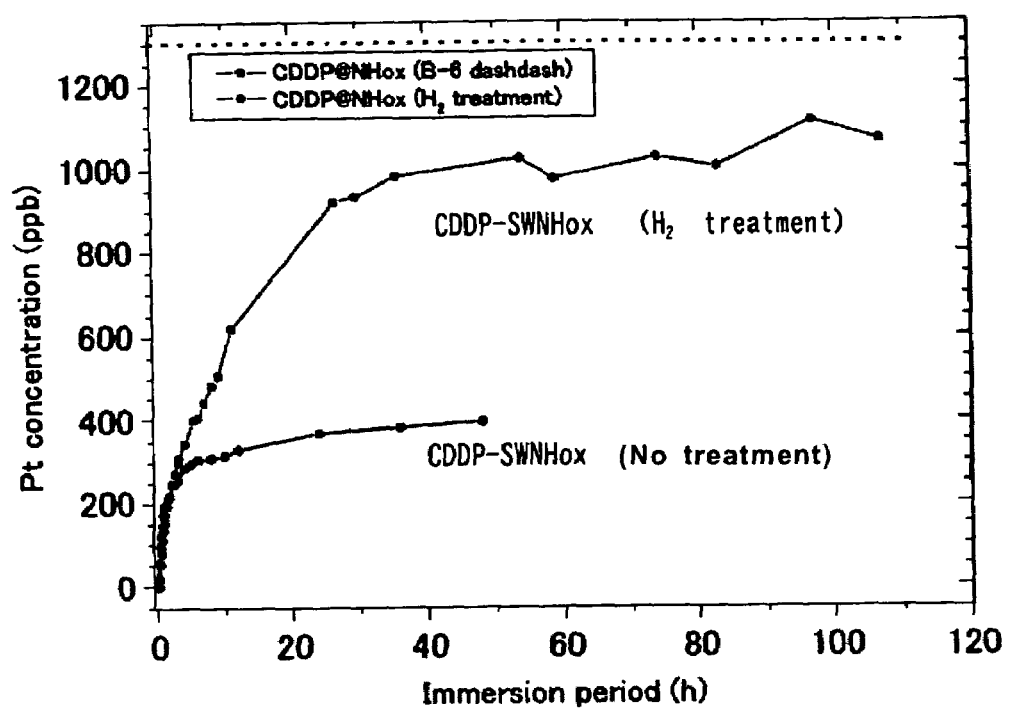
FIG. 13 shows the result of measurement for amount of CDDP released into saline from CDDP-CNHox complex.

FIG. 13 shows the result of measuring the release of CDDP from CDDP-CNHox complex into the physiological saline. As shown, the amount of the release increases in accordance with the immersion time in physiological saline. The release speed was relatively fast, when CDDP was included after the treatment of CNHox in hydrogen at 1200° C. for 1 hour. In contrast, when CNHox itself was used, the release speed was particularly slow and the sustained release effect was remarkable. The release amount reached to 1350 ppb (shown with a dashed line) when all the included CDDP were released.

<2> In vitro Assay for Cancer Cell Viability

The effect of CDDP released from CNHox was examined using the WST-1 assay. The CDDP-CNHox powder was added to human derived lung cancer cells NCI-H460. CDDP is a drug which has a effect on human lung cancer. These cells were maintained in RPMI-1640 medium containing 5% FBS at 37° C. in a humidified atmosphere with $CO_2$ and air. For these cells, CDDP-CNHox or CDDP or CNHox was added respectively, and after the addition, each sample was examined. NCI-H460 cells were seeded at 4,000 cells/well and were cultured for 43 hours. Meanwhile, the cells were cultured for 67 hours when seeded at 2,500 cells/well (no addition of CDDP-CNHox or CDDP). And then it was confirmed that the NCI-H460 cells were extinct by drug addition. The amount of the extinct NCI-H460 cells was estimated by observing the decrease in the emission intensity to indicate the absorbency of formazan (with blue dye) showing the living of cells. And also, the NCI-H460 cells were directly observed using the optical microscope.

Figure 14A:
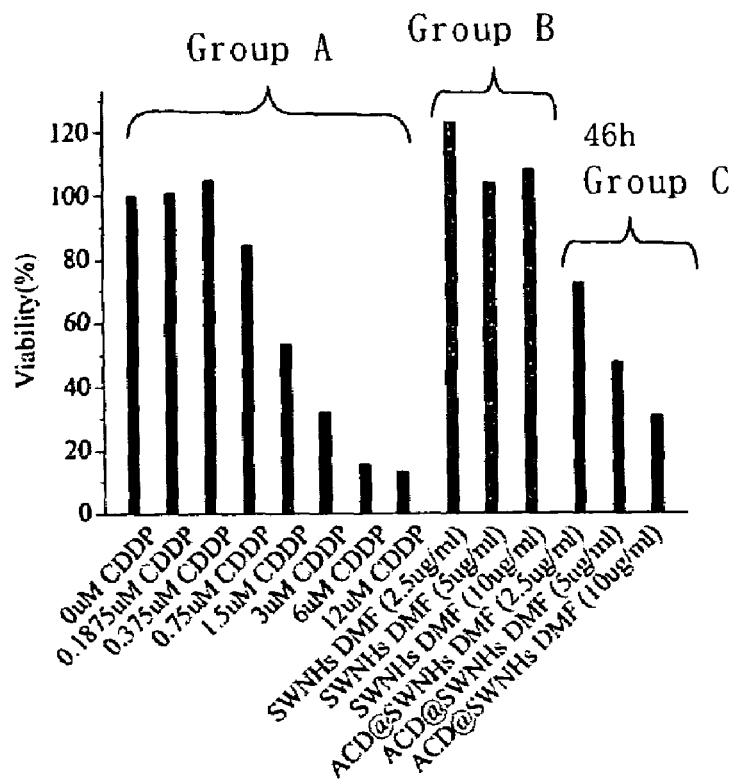
FIGS. 14A and 14B show the viability rate of NCI-H460 cells after drug addition (Culture periods of FIGS. 14A and 14B are 46 and 72 hours, respectively).
Figure 14B:
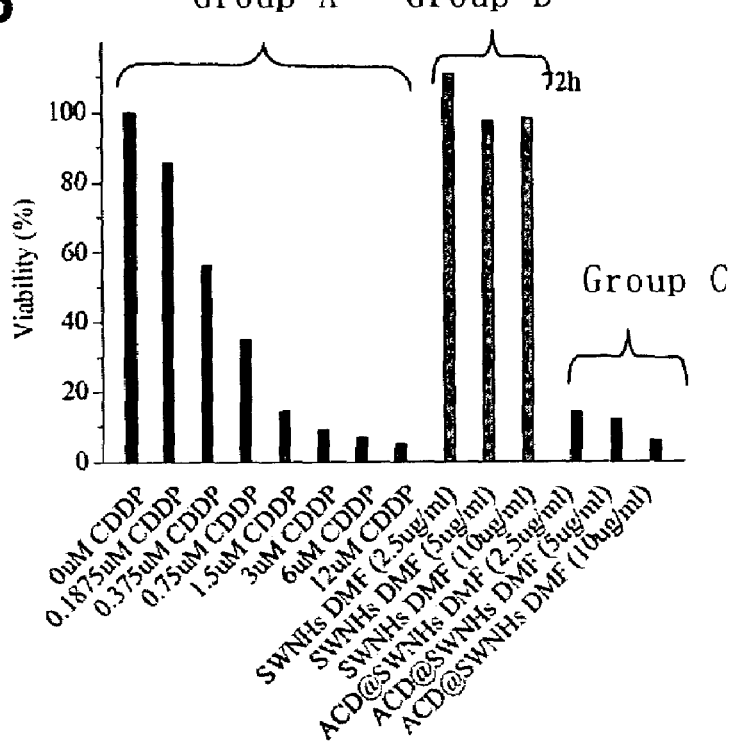

FIGS. 14A and 14B show the viability rate of NCI-H460 cells under drug addition (incubation time: FIG. 14A is 46 hours, FIG. 14B is 72 hours). Group A in the figures shows the result of adding CDDP, and the viability rate of NCI-H460 cells was decreased dose-dependently. In other words, NCI-H460 cell extinction rate by the apoptosis was increased in accordance with the increase of the dosage. Groups B and C in the figures show the results of adding CNHox and of adding CDDP-CNHox, respectively. These results show that the cell viability was decreased dose-dependently in group C as well as in group A, but not decreased in group B.

Above results were observed using the optical microscope. Those results are shown in FIGS. 15A-15C and FIGS. 16A-16C.

Figure 15A:
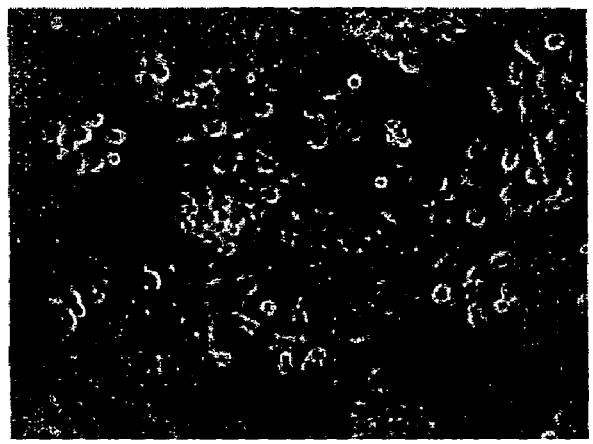
FIGS. 15A, 15B and 15C show the results of observation about the living of NCI-H460 cells after 46-hour incubation, using light-optic microscopy (FIG. 15A shows the result of no drug addition, FIG. 15B shows the result of CNHox addition, and FIG. 15C shows the result of CDDP-CNHox (containing CDDP 3.8 µM) addition).
Figure 15B:
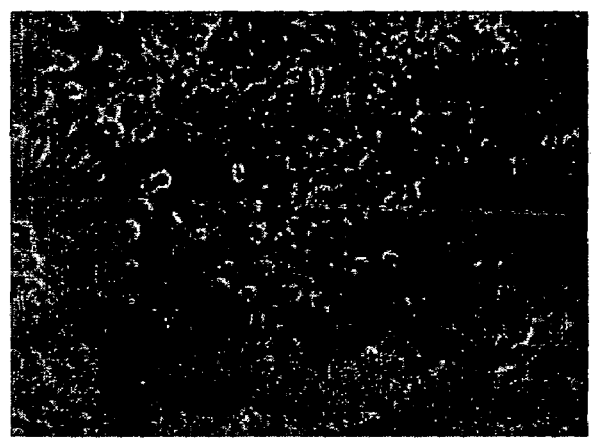
Figure 15C:
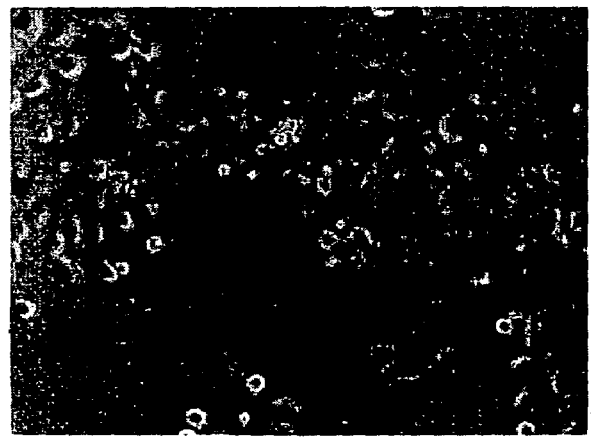
Figure 16A:
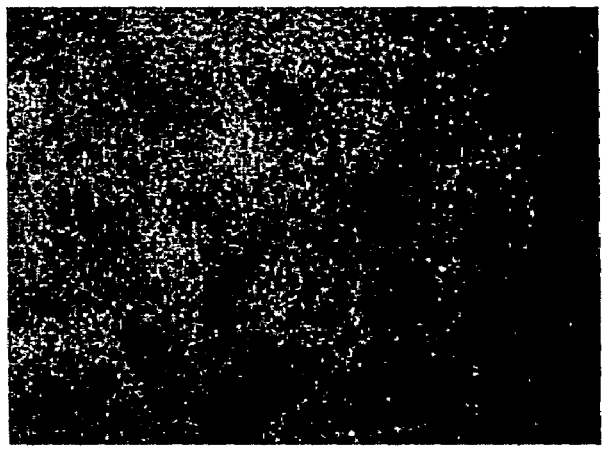
FIGS. 16A, 16B and 16C show the results of observation about the living of NCI-H460 cells after 72-hour incubation, using light-optic microscopy (FIG. 16A shows the result of no drug addition, FIG. 16B shows the result of CNHox addition, and FIG. 16C shows the result of CDDP-CNHox (containing CDDP 3.8 µM) addition).
Figure 16B:
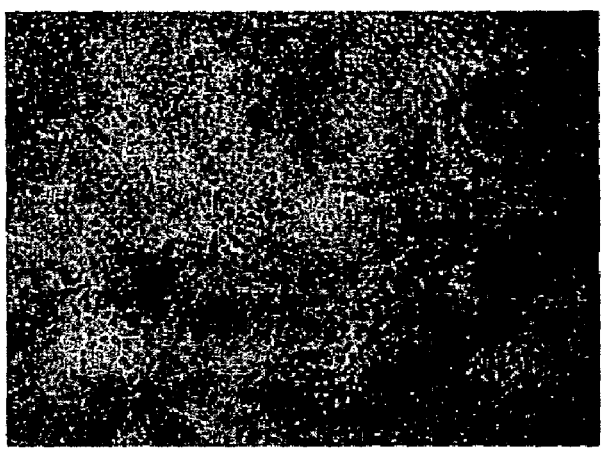
Figure 16C:
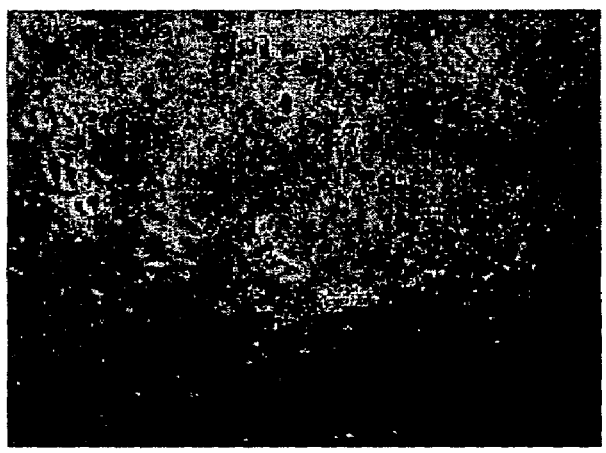

FIGS. 15A and 16A show the results of no drug addition, FIGS. 15B and 16B show the results of CNHox addition, and FIGS. 15C and 16C show the results of CDDP-CNHox (containing CDDP 3.8 μM) addition. The results after 46 hour-incubation are shown in FIGS. 15A, 15B and 15C. The NCI-H460 cell number in FIG. 15C was less than the number in FIGS. 15A and 15B. FIGS. 16A, 16B and 16C show the results after 72 hour-incubation. The NCI-H460 cell number in FIG. 16C was remarkably less than the number in FIGS. 16A and 16B. These results indicate that the growth of NCI-H460 cells has been inhibited by CDDP-CNHox addition.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A complex of drug and carbon nanohorns, which complex comprises a metal-containing anti-cancer drug being adsorbed onto or included in oxidized porous carbon nanohorns.

2. The complex of claim 1, exhibiting a sustained release of the drug into an aqueous solution of phosphate-buffered saline.

3. The complex of claim 1, wherein the drug is a platinum or iron coordination compound.

4. The complex of claim 1, wherein the metal-containing drug comprises cisplatin.

5. The complex of claim 1, wherein the metal-containing drug comprises bleomycin.

* * * * *